United States Patent [19]

Nair

[11] Patent Number: 5,912,251
[45] Date of Patent: Jun. 15, 1999

[54] METABOLICALLY INERT ANTI-INFLAMMATORY AND ANTI-TUMOR ANTIFOLATES

[76] Inventor: Madhavan G. Nair, 7005 Charleston Oaks Dr. N., Mobile, Ala. 36695

[21] Appl. No.: 09/008,613

[22] Filed: Jan. 17, 1998

[51] Int. Cl.[6] ........................ C07D 239/95; A61K 31/505
[52] U.S. Cl. ............................................ 514/260; 544/291
[58] Field of Search ............................... 514/260; 544/291

[56] References Cited

U.S. PATENT DOCUMENTS

| | | | |
|---|---|---|---|
| 4,996,207 | 2/1991 | Nair et al. ................................ | 514/258 |
| 5,550,128 | 8/1996 | Nair et al. ................................ | 514/249 |
| 5,593,999 | 1/1997 | Nair et al. ................................ | 514/260 |

FOREIGN PATENT DOCUMENTS 0239362  of 1987  European Pat. Off. .

OTHER PUBLICATIONS

A. Rosowsky, H. Bader and J.H. Freisheim J. Med. Chem. 34, 203–208 (1991).
Nair, et al. J. Med. Chem. 34, 222–227 (1991).

*Primary Examiner*—John M. Ford

[57] ABSTRACT

Hether to unknown metabolically inert classical folate analog inhibitors of the enzyme Dihydrofolate Reductase [DHFR] that are transported to tumor cells via the reduced folate receptors are provided. These compounds exhibit superior anti-asthmatic responses in rabbits relative to methotrexate and the standard drug theophylline. The title compound 4-amino-4-deoxy-5,8,10-trideaza-pteroyl-4'-methyleneglutamic acid (1) exhibited outstanding anti-tumor activity. Compound 1 was 1,000 to 10,000 times more active than methotrexate in causing total growth inhibition (TGI) of a number of human tumor cells in culture. Unlike methotrexate the the TGI values of 1 are in the range of therapeutically relevant concentrations. Tumor cells that are resistant to methotrexate by virtue of defective polyglutamylation were 3–4 times more collaterally sensitive to compound 1. 1 was completely inert on incubation with folylpolyglutamate synthetase. On treatment of 1 with a preparation of aldehyde oxidase no oxidative activity was uncovered. Compound 1 was totally resistant to hydrolytic cleavage of the glutamate moiety by carboxypeptidase derived from Pseudomonad sp. These biochemical and pharmacological properties of the metabolically inert classical antifolates establish their clinical utility and superiority as new and novel anti-inflammatory and anti-tumor agents exhibiting enhanced target enzyme specificity and lower toxicity.

32 Claims, No Drawings

METABOLICALLY INERT ANTI-INFLAMMATORY AND ANTI-TUMOR ANTIFOLATES

FIELD OF INVENTION

This invention relates to folic acid antagonists that are metabolically inert exhibiting a high level of anti-inflammatory and anti-tumor activity. Metabolically inert classical antifolates are new and therefore they exhibit unexpected biological properties such as those recited in this invention. The field of this invention is confined to the anti-inflammatory, anti-neoplastic and anti-rheumatoid activity of new and novel folate antimetabolites.

The compound numbers identify the same compounds they identify in all descriptions.

BACKGROUND OF THE INVENTION

Antifolates are compounds that interfere at various stages of folate metabolism [M. G. Nair. "The Chemistry of Antitumor Agents". Chapter, 7; Blackie & Sons. London. 1991]. Folate is a vitamin that is essential for the biosynthesis of purine and pyrimidine nucleotide precursors of DNA. Therefore antifolates are capable of inhibiting DNA biosynthesis and hence cell division. Indeed methotrexate (MTX) which is a powerful antifolate by virtue of its inhibition of Dihydrofolate Reductase (DHFR) mediated production of the active vitamin tetrahydrofolate is curative to Choriocarcinoma and Burkitt's lymphoma. MTX is also widely used as a single agent or in combination with other drugs for the treatment of various forms of human cancers [M. G. Nair. "Cancer Growth and Progression: Cancer Management in Man" Volume 10, H. E. Kaiser (Ed); Kluwer Academic Publishers, Chapter, 7, 1989]. The anti-rheumatoid properties of MTX is well documented and it is currently used as an arthritis remittive agent under the trade name Rheumatrex. MTX has also shown activity against asthma, but it has not yet been used clinically for this indication, except on an experimental basis.

In 1973 Nair and Baugh [Biochemistry, 12, 3923, 1973] discovered that MTX is metabolized to its polyglutamyl derivatives in human and other mammalian tissues. Once formed within the cells, MTX polyglutamates do not readily efflux and they remain for long periods exerting their cytotoxic effects to tumor and normal cells. This prolonged retention of MTX polyglutamates relative to MTX results in the potentiation of host toxicity. In 1991 Nair discovered that [U.S. Pat. No. 5,073,554] contrary to the widely accepted notion, polyglutamylation of classical antifolates is not essential for anti-tumor activity and in fact this metabolic transformation may indeed cause the loss of pharmacological control and target specificity of the drug. This new finding resulted in the discovery of a number of non-polyglutamylatable classical antifolates and led to the clinical development of methylene-10-deazaaminopterin [MDAM] as an experimental anticancer drug for the treatment of human solid tumors [Clinical Cancer Research, 2, 707–712, 1996]. In 1996 Nair and coworkers identified [U.S. Pat. No. 5,550,128] the active enantiomer of MDAM as the one that possess the L-configuration [L-MDAM]. Further investigation by Nair and coworkers to delineate the metabolic disposition of certain non-polyglutamylatable antifolates led to the unexpected finding that the presence of the 4-methyleneglutamate moiety modulates the binding of such compounds to the liver enzyme aldehyde oxidase which mediates their oxidative deactivation to the corresponding 7-hydroxy derivatives [Cellular. Pharmacology, 3, 29, 1996].

Another in vivo transformation of MTX is the cleavage of the C9-N10 bond during its entry to the enterohepatic circulation. The cleaved products are inactive and therefore constitutes an alternate pathway of metabolic inactivation. It has also been documented that the intestinal microflora are capable of removing the L-glutamate portion of methotrexate and aminopterin to inactive compounds that enter systemic circulation via enterohepatic circulation and further adversely complicate the biochemical pharmacology of these drugs. Taken together, these multiple pathways of drug inactivation and the formation of the 7-hydroxyderivative, its competition with the parent drug for polyglutamylation and transport to target cells and the loss of target specificity secondary to the above metabolic transformation not only undermine the pharmacological control of MTX but also results in loss of efficacy and manifestation of undesirable toxicity.

As part of a continuing program aimed at the development of less toxic and more specific antifolate drugs for the treatment of human cancers, the pteridine ring of the experimental anticancer drug methylene-10-deazaaminopterin [MDAM] was replaced with a quinazoline ring. This new compound 1 when evaluated for its potential utility as an antitumor agent using a number of biological test systems exhibited unexpected biological properties. For example 1 was completely inert when incubated with rabbit liver aldehyde oxidase establishing that it is not converted to the corresponding 7-hydroxy derivative. Compounds 1 and 1d on incubation with carboxypeptidase derived from Pseudomonad sp failed to remove the 4-methyleneglutamate moiety establishing that it is resistant to microbial inactivation by intestinal flora. Further, and perhaps due to the total inertness of 1 to metabolic transformation, unlike other classical antifolates 1 was able to kill a large number of human luekemia and human solid tumor cells in culture at therapeutically relevant concentrations. Since compound 1 has a methylene group as opposed to the methylamino group of MTX at the tenth position it is also not subject to bacterial deactivation by cleavage of the bridge bond. When evaluated for inhibitory activity against the growth of a number of human cancer cells in culture, compound 1 was strikingly more active than either MTX or MDAM. Further evaluation in vitro using the enzyme folylpolyglutamate synthetase revealed that 1 and its analogs reported herein are not capable of elaboration to its polyglutamates due to the presence of the 4-methyleneglutamate moiety. There fore the unexpected enhanced biological activity of 1 must have its origin in the complete lack of its in vivo metabolism [FIG.-1]. Unlike trimetrexate, the compounds described in this invention are capable of transport to target tumor cells by the reduced folate transporter (RFT) due to the presence of the 4-methyleneglutamate moiety. More strikingly, compound 1 was 4–5 times collaterally more sensitive in inhibiting the growth of leukemia cells that are resistant to MTX by virtue of defective polyglutamylation compared to the wild type MTX sensitive parental CCRF-CEM cell line. Accordingly, this invention demonstrates that metabolically inert classical folate analog inhibitors of dihydrofolate reductase are superior antitumor agents relative to the metabolizable classical antifolates such as methotrexate and aminopterin and to the 7-hydroxylatable but non-polyglutamylatable antifolates MDAM and MEDAM. As a model of metabolically ineffective DHFR inhibitor, compound 1 was evaluated as a potential anti-inflammatory agent relative to MTX and surprisingly it exhibited outstanding activity in this animal model of asthma substantiating the superiority of metabolically inert DHFR inhibitors. In fact 1 was found to be not only superior to MTX but also to the well known anti-asthmatic drug theophylline in both early and late asthmatic responses and bronchial hyper responsiveness (BHR) when evaluated using allergic rabbits. The anticancer and anti-inflammatory antifolates reported in this invention include close analogues of 1 bearing modified C9–10 region incapable of aldehyde oxidase mediated 7-hydroxylation and the 4-methyleneglutamate moiety that prevents polyglutamylation and modulation of binding to aldehyde oxidase. These quinazoline-based compounds [1, 1a, 1b, 1c, and 1d ] may possess the racemic D,L-4-methyleneglutamate, enantiomerically pure D-4-methyleneglutamate ["D" configuration ] or enantiomerically pure L-4-methyleneglutamate ["L" configuration ] moieties. They are also useful for the treatment of rheumatoid arthritis due to their inhibition of the enzyme dihydrofolate Reductase.

This invention accordingly provides a process for treating neoplastic diseases [leukemia, ascetic and solid tumors ], a process for treating asthma and related inflammatory diseases and a process for treating rheumatoid arthritis and other auto immune diseases which comprises administering to a warm blooded animal with an abnormal proportion of leukocytes or other evidence of neoplastic disease, asthma or rheumatoid arthritis a therapeutically effective non-toxic amount of 5,8,10-trideaza-4'-methyleneaminopterin (1) [herein referred to as compound 1] or its close analogues 1a–1d as such or in the form of a pharmacologically acceptable salt thereof. They may be combined with other compounds such as leucovorin [folinic acid; citrovorum factor] to reduce toxicity or in combination with other anticancer drugs including but not limited to tomudex, 5-FU; 5-FdUR; carboplatin, oxaloplatin or cis-platin; taxol, campothecins or cyclophosphamide to enhance efficacy.

The salts of 1 or its close analogues [1a–1d] may be formed with one or more of the amino groups of the quinazoline ring with acids such as acetic, hydrochloric, sulfuric, sulfonic, nitric, hydrobromic, phosphoric, citric, salicylic or methanesulfonic. Compound 1 or its close analogues and salts thereof may be administered to a warm blooded animal by oral or parenteral (intraperitoneal, intravenous, intrathecal, subcutaneous, intramuscular, etc.) routes. Higher dosage of 1 or its close analogues [1a–1d ] may be administered in conjunction with racemic leucovorin [6-(R,S) 5-formyltetrahydrofolate] and/or folic acid to further reduce toxicity.

Compound 1 or its close analogues [1a–1d ] may be provided in composite forms to facilitate administration to patients or in dosage unit form. A non-toxic and sterile carrier may be added to 1 and its close analogues. This carrier may be solid, liquid or semi-solid that may serve as a medium, vehicle or excipient. Methyl cellulose, polyhydroxybenzoate, talc, gelatin, lactose, dextrose, starch, mannitol, sorbitol, mineral oil, gum acacia, oil of theobroma or magnesium stearate may serve as a carrier. Another useful and preferred formulation of these entities for administration to patients is their conversion to the corresponding sodium or potassium salts by dissolving in either sodium bicarbonate, potassium bicarbonate, sodium carbonate or potassium carbonate solution. The resulting solutions may be used as such or cryodessicated to the solid sodium or potassium salt and conveniently formulated in aqueous or non-aqueous vehicles or carriers. Compound 1, or its close analogues (1a–1d) and a carrier or diluent can be encapsulated or enclosed in a paper or other container, cachet, gelatin, capsule or sachet when intended for use in dosage units.

The process of the invention for the synthesis of compound 1 starts with the conversion of commercially available 5-methyl-2-nitrobenzoic acid to the corresponding amide 2 and its subsequent transformation to 5-methyl-2-nitrobenzonitrile (3) by standard procedures. Reaction of 3 in DMF under nitrogen with p-formylmethylbenzoate in presence of an organic base such as diazabicyclo octane for several hours gave the olefin (4) after work up as a mixture of geometric isomers. Olefin 4 can also be prepared by reacting 3 with p-formylmethylbenzoate in methanol using sodium methoxide as a base. In general this reaction can be performed in any appropriate organic solvents using commonly used organic or inorganic bases. Reduction of 4 with sodium dithionite gave the aminonitrile (5) which was cyclized with guanidine to the corresponding pteroate analogue (6) which after catalytic hydrogenation and hydrolysis gave 4-amino-4-deoxy-5,8,10-trideazapteroic acid (2). Coupling of 7 with diethyl-4-methyleneglutamate by the isobutylchloroformate method previously described by Nair and Baugh [Biochemistry, 12,3923–3927, 1973] followed by mild hydrolysis of the resultant diester gave crude 1 which was purified by reverse phase chromatography on C-18 silica gel using 12% acetonitrile in water as the eluting solvent [Scheme-1].

An alternate procedure for the preparation of olefin 4 is allylic bromination of 3 to the corresponding benzyl bromide (3b), and its subsequent reaction with triphenylphosphine to the wittig salt. Treatment of thisWittig salt with p-formylmethylbenzoate in an organic solvent (eg, DMF) using an organic base in a typical Wittig reaction gave 4 in moderate yield. Any covenient organic solvent and an organic or inorganic base compatable with the solvent can be used for this reaction.

Substitution of p-formyl methylbenzoate with p-carbomethoxyacetophenone in the above reaction with 3 gives the corresponding methyl substituted olefin which after dithionite reduction, guanidine cyclization, hydrogenation, hydrolysis, diethyl-4-methyleneglutamate coupling followed by mild hydrolysis yields the 10-methyl derivative 1a. Likewise substitution of p-formyl methylbenzoate with p-carbomethoxypropiophenone in the reaction with 3 and workup as above should yield the 10-ethyl derivative 1b.

Benzylic bromination of 3 gave the corresponding bromomethyl derivative(3b) that on reaction with p-methylaminomethybenzoate and methyl-p-methylaminobenzoate gave the corresponding aminonitriles which after dithionite reduction, guanidine cyclization and hydrolysis gave the pteroate analogs 8 and 9. 4-Methyleneglutamate coupling described as above and hydrolysis gave the 10-nor-methylamino and 10-nor-amino derivatives 1c and 1d respectively.

In order to unravel the mechanism of action of 1 and 1 e they were examined as inhibitors of human dihydrofolate Reductase. Both compounds exhibited inhibitory activity to this enzyme similar to that of MTX. The $I_{50*}$ values for the human enzyme by 1, 1e and MTX were 66.0, 66.0 and 11.0 nM respectively. The corresponding value for trimetrexate (TMTX) was 54.0 nM.

EXAMPLE-1

Evaluation of Asthmatic Responses and Bronchial Hyper Responsiveness

Experimental Model: Induction of Asthma in Rabbits. New Zealand White Pasturella-free rabbit litter mates were bred and immunized ip within 24 hour of birth with 312 AU dust mite allergen extract [Berkeley Biological, Berkeley, Calif.] in 10% kaolin once every week for one month, then biweekly until the age of 4 months. Mustafa and co-workers used this rabbit model as described in American Journal of Physiology [266, 271–277, 1994]. These allergic animals preferentially produce allergen-specific IgE antibody and typically respond to aeroallergen challenge with an early and late phase asthmatic response and show increased bronchial hyper responsiveness (BHR).

Allergen, Theophylline and Antifolate Challenges: These experiments were carried out as described by Mustafa and co-workers in the Journal, Agents and Actions in 1992 [37, 168–170, 1992 ]. Briefly, allergic rabbits were challenged with ragweed allergen aerosol (10,000 PNU/mL) as described until there was an approximate 50% reduction in dynamic compliance (Cdyn). Pulmonary function was measured at 15 minutes intervals for 6 hours. The rabbit was challenged with indicated antifolates [5 mg/mL, aerosolized for 4 minutes ] followed immediately by the same total dose of allergen. Pulmonary function measurements as described by Mustafa and co-workers in the cited reference were carried out for 6 hours. A repeat histamine challenge was performed 24 hour later to determine the effect of MTX, theophylline and I on allergen induced bronchial hyper responsiveness.

To assess the effect of antifolates on allergen-induced changes in the airways, the area under the curve for early and late -phase response was digitalized by computer-assisted plenometry for each rabbit during the six hour time period. The results are summarized in table-1.

TABLE 1

Comparative Effects of MTX and 1e on Allergen-induced Asthmatic Responses and Bronchial Hyper-responsiveness (BHR) in Allergic Rabbits [percent inhibition from control]

| Compound | Asthmatic Response | | BHR |
| --- | --- | --- | --- |
| | Early | Late | |
| MTX | 29 | 37 | 32 |
| 1 | 52 | 58 | 47 |
| Theophylline | 45 | 49 | 39 |

MTX and 1 were given as aerosol (5 mg/ml). Theophylline was given as aerosol (5 mg/ml)

EXAMPLE-2

Commercially available 5-methyl-2-nitrobenzoic acid was converted to its corresponding amide by reaction with isobutylchloroformate and then ammonia. The resultant amide was converted to 5-methyl-2-nitrobenzonitrile (3) by $POC_3$ in DMF.

Preparation of 4

In a round bottomed flask a mixture of 6.6 gr (40 mmol) of 3 and 6.5 gr (~40 mmol) of 4-formylmethylbenzoate were dissolved in 75 mL of methanol and under stirring 40.8 mmol of a solution of sodium methoxide was slowly added. The mixture was stirred for 72 hrs whereupon a bright yellow precipitate was formed. At this stage the reaction mixture was acidified with acetic acid, evaporated, and triturated with 100 gr of ice. The resultant bright yellow precipitate of 4 was filtered, washed sucessively with water, methanol and dried. Yield 5.8 gr; mp 266–269° C.; MS (FAB),[$C_{17} H_{12} N_2 O_4$], calcd, 308; found 309 [MH+].

Benzylic bromination of 5-methyl-2-nitrobenzonitrile by NBS by the standard procedure followed by treatment of the resultant product (3b) with triphenylphosphine gave 3-cyano-4-nitrobenzyltriphenylphosphonium bromide in good yield.

Wittig Reaction of 3-cyano-4-nitrobenzyltriphenylphosphonium bromide with p-formylmethylbenzoate. Alternate Synthesis of 4.

To a stirring solution of 8 mmol [4.025 gr] of the phosphonium bromide (3b) and 8 mmol [1.315 gr] of p-formylmethylbenzoate in 30 mL DMF under nitrogen was added 1.2 mL of DBN portion-wise during a period of 15 minutes and the red solution was allowed to stir for 4 days. Addition of 50 mL of absolute ethanol gave a yellow precipitate of 4 that was filtered, washed with water and again with absolute alcohol. yield, 1.6 gr.

EXAMPLE-3

Dithionite Reduction of Product 4 of Example-2: To a stirring solution of 1.0 gr of 4 in 40 mL of DMF maintained between 60–70 degrees was added portion-wise 5.0 gr of sodium dithionite followed by the addition of 60 mL of water during 20 minutes. About 15 minutes after the addition was complete, the mixture was evaporated to dryness under reduced pressure and 25 gr of ice was added whereupon a pink solid was formed. After all the ice had melted the precipitate was filtered, washed with water and dried to obtain 700 mg of the product. The reduction product showed a single spot on a TLC plate which was more polar than the starting compound. mp, 195–197° C.; MS [$C_{17} H_{14} N_2 O_2$], Calcd, 278; Found, 279 [MH+].

EXAMPLE-4

Guanidine Cyclization of the Dithionite Reduction Product of Example-3: Metallic sodium [70.0 mg] was dissolved in 15 mL of ethoxy ethanol and the resultant solution was mixed with a solution of 287 mg of guanidine hydrochloride in 15 mL of the same solvent, filtered and added to 556 mg of the above dithionite reduction product placed in a 100 mL round bottomed flask fitted with a solvent adapter. The mixture was slowly heated under stirring to reflux using a silicone oil bath during a period of two hours and the reflux continued till all the solvent was boiled off from the flask. the residue was kept in the oil bath at 190–200° C. for 30 minutes and then removed from the bath. Addition of 50 mL ether and trituration gave a solid which was filtered, washed with water and dried. Repeated washing of the product with 8% methanol in methylene chloride gave the crude cyclization product 6. Yield, 150 mg. mp.>300° C.; MS [$C_{18} H_{16} O_2 N_4$] Calcd, 320; Found 321 [MH+]

EXAMPLE-5

Preparation of 4-amino-4-deoxy -5,8,10-trideazapteroic acid (7). The cyclization product [200 mg] was dissolved in 35 mL of DMF and hydrogenated for 48 hours at a hydrogen pressure of 20 psi with 50 mg of 10% palladium on carbon as a catalyst. The catalyst was removed by filtration and the filtrate was evaporated to dryness to obtain a solid which was stirred with a mixture of 50 mL of 0.1 N NaOH and 20 mL of acetonitrile for 18 hours. Acetonitrile was removed by rotary evaporation and the clear solution thus obtained was acidified with glacial acetic acid to pH 4.0 and chilled in the refrigerator overnight, filtered, washed with water and dried. Yield 65 mg, MS [C17 H16 N4 O2] Calcd, 308; Found 309 [MH+]. Alternately, the cyclization product can be hydrolysed first and then hydrogenated to 7.

EXAMPLE-6

Preparation of 4'-Methylene-5,8,10-trideazaaminopterin (1): A solution of 1 mmol (308 mg) of 4-amino-4-deoxy-5, 8,10-tridezapteroic acid in 50 mL of DMF was cooled in an ice-bath and was added 1.25 mmol of triethylamine followed by 1.0 mmol of isobutylchloroformate. After 15 minutes the round bottomed flask containing the solution was removed from the ice-bath and allowed to warm up to room temperature during one hour. To this mixed anhydride a solution of 2.0 mmol of diethyl-4-methyleneglutamate hydrochloride dissolved in 15 mL of DMF and which was neutralized with 2.0 mmol of triethylamine was added and the reaction mixture allowed to stir for 18 hours and evaporated under reduced pressure On trituration with 75 gr of ice a brownish yellow precipitate was formed which was filtered, washed with water and suspended in a mixture of 100 mL of 0.1 N NaOH and 35 mL of acetonitrile and stirred overnight. The reaction mixture was evaporated to ~60 mL under reduced pressure at 40° C., cooled in an ice-bath and acidified to pH 4.0 with glacial acetic acid whereupon a bright yellow precipitate was formed. This precipitate was collected by filtration, washed with water and dissolved in minimum amount of 5% sodium bicarbonate and chromatographed using a C-18 silica gel column made in 12% acetonitrile in water and eluting with the same solvent. All fractions corresponding to the product were pooled and acidified to pH 4.0 with glacial acetic acid to obtain 1 as a precipitate which was filtered, washed with water and dried. Yield 125 mg. mp>250° C.; MS [$C_{23} H_{23} N_5 O_5$]; Calcd, 449; Found, 450 [MH+]

Anti-tumor activity of 4-amino-4-deoxy-5,8,10-tridezafolate (1).

Compound 1 was evaluated for its anti-tumor activity using the Human Disease Oriented in vitro Antitumor Screen at the National Cancer Institute. Surprisingly 1 unlike other antifolates was able to kill cancer cells with remarkable potency. This unexpected finding may be due to the inability of 1 to undergo metabolic transformation. The total growth inhibition [TGI] of selected human tumor cells by 1 relative to methotrexate (MTX) is presented in Table-2. A log 10 TGI value of less than –4.0 is therapeutically non-relevant for MTX. The data in table-2 show that 1 is at least 1,000–10,000 times more effective than MTX in this panel and the values represent therapeutically relevant concentrations.

TABLE 2

Total Growth Inhibition (TGI) of Selected Human Tumor Cells by Compound 1 and MTX

| Cell line | Compound 1 Log 10 TGI | MTX LOG 10 TGI |
| --- | --- | --- |
| Leukemia | | |
| CCRF-CEM | <–8.00 | –3.77 |
| K562 | <–8.00 | –3.3 |
| MOLT-4 | –7.4 | –3.55 |
| RPMI 8226 | –7.44 | –3.66 |
| SR | <–8.00 | –3.25 |
| CNS Cancer | | |
| SF 539 | –6.3 | –3.66 |
| Breast Cancer | | |
| MCF7 | –6.32 | — |
| MCF7-ADR-RES | –7.26 | — |

EXAMPLE-7

Preparation of 5,8-dideazamethotrexate (1d)

a) Reaction of 5-bromomethyl-2-nitrobenzonitrile with methyl-4-methylaminobenzoate.

A suspension of 325 mg of the bromo compound from example-1, 330 mg of methyl-4-aminomethylbenzoate and 65 mg of magnesium oxide in 5.0 mL of dimethylacetamide was heated under stirring at 80° C. for 6 hrs. To this mixture was added 30.0 mL of EtOAc and filtered. The filtrate was washed with water repeatedly three times, dried over sodium sulfate and evaporated to obtain a solid which was tirturated with 20.0 mL of ether and filtered. The product was homogeneous on TLC and melted at156–160 C. Yield, 230 mg. MS, [$C_{17} H_{15} N_3 O_4$], Calcd, 325; Found, 326 [MH+].

b) Dithionite Reduction: The product [2.3] gr obtained as in example 7-a was dissolved in 300 mL of DMF at 65 C in an Erlenmeyer flask containing a magnetic stirrer and placed in a water bath which was maintained at 65–70 C. Under stirring to this solution was added 10.0 grams of sodium dithionite and 300 mL of water during 25 minutes. An additional 300 mL of water was then added and the mixture placed in an ice-bath and stirred. After one hr the yellow solid that separated was collected by filtration washed with water and dried, mp; 140–41° C.; Yield, 1.5 gr; MS, [$C_{17} H_{17} O_2 N_2$], Calcd, 295; Found 296.

c) Cyclization and Hydrolysis of the Dithionite Reduction Product: The dithionite reduction product of example 7-b was treated with 1.25 equivalents of guanidine base [generated from 1.5 equivalents of guanidine hydrochloride and an equimolar amount of sodium in ethoxy ethanol(200 mL)] and placed in an oil bath maintained at 180–200° C. The ethoxy ethanol was allowed to boil off and the residue kept at 200° C. for 20 minutes and then removed from the oil bath. After cooling to ambient temperature, 250 mL of ether was added and triturated to obtain a dark brown solid that was filtered, washed with ether and stirred with a mixture of 250 mL of 0.1 N NaOH and 80 mL of acetonitrile for 18 hrs. The clear solution thus obtained was evaporated to ~200 mL, acidified to pH, 8.0 with 1 N, HCl and re evaporated under reduced pressure to ~75 mL, chilled and acidified with glacial acetic acid whereupon a dark yellow solid of 8 was separated which was filtered, washed with water and dried in vacuum. Yield, 750.00 mg; MS [$C_{17} H_{17} N_5 O_2$], Calcd, 323; Found 324 [MH+].

d) Diethyl-4-methyleneglutamate Coupling: A solution of 323 mg [1.0 mmol] of 4-amino-4-deoxy-5,8-dideaza-10-methylpteroic acid (8) obtained as above from example-7c was dissolved in 45 mL of dry DMF. This solution was cooled in an ice-bath and was added under stirring 1.25 mmol of triethylamine followed by 1.0 mmol of isobutylchloroformate. After allowing to warm up to room temperature a solution of 2.0 mmol of 4-methyleneglutamate hydrochloride and 2.0 mmol of triethylamine was added and the reaction mixture was allowed to stir for 18 hrs and evaporated under reduced pressure. The viscous product thus obtained was stirred with 25 mL of 5% sodium bicarbonate and filtered. After washing with water the solid was hydrolyzed with a mixture of 50 mL of 0.1 N NaOH and 20 mL of acetonitrile for 16 hrs, evaporated to ~30 mL, cooled in an ice-bath and acidified with glacial acetic acid to pH 4.0 to obtain a brown precipitate of Id which was washed, re-dissolved in 10.0 mL of 5% sodium carbonate and chromatographed on a C18 silica gel column using 12% acetonitrile in water as the eluting solvent. The major fractions corresponding to the desired product was pooled and acidified with acetic acid to obtain a yellow precipitate which was filtered, washed with water and dried in vacuum. Yield 120 mg.; MS, [C23 H24 N6 O5], Calcd, 464; Found, 465 [MH+]

Fig 1: Illustration of Metabolic/Catabolic Block in Compound 1.
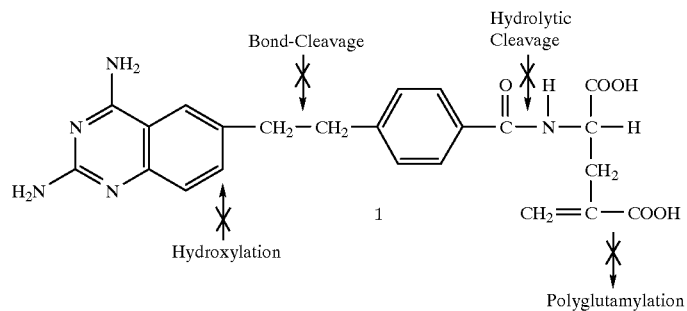
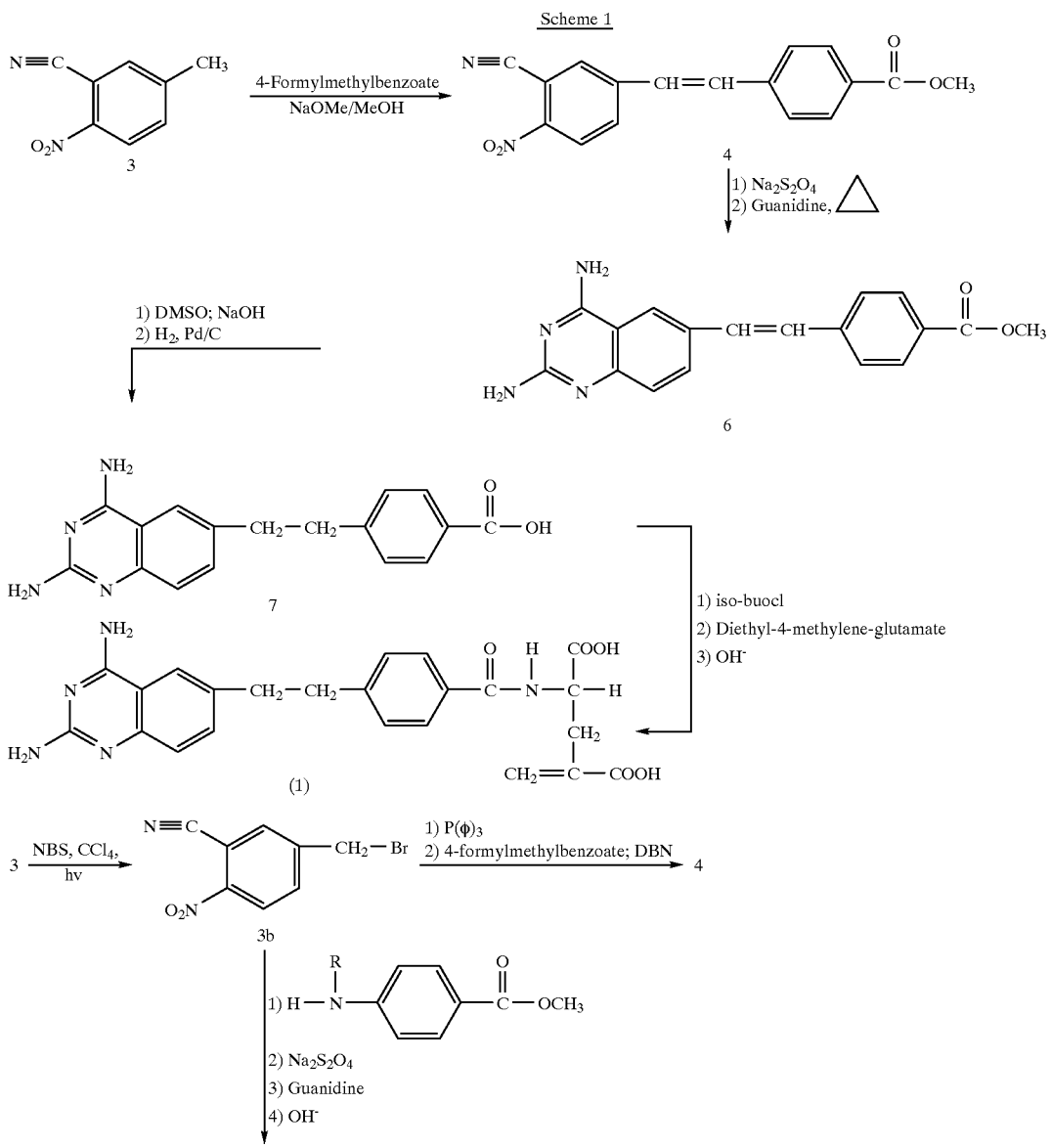

-continued

1c R = -H  ←Steps← 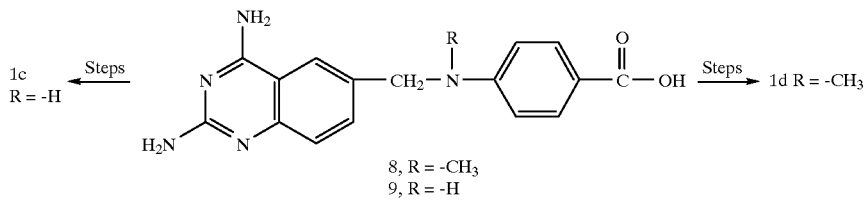 →Steps→ 1d R = -CH₃

8, R = -CH₃
9, R = -H

Having regard to the foregoing disclosure, the following is claimed as inventive and patentable embodiments thereof:

1. 4-Amino-4-deoxy-5,8,10-trideazapteroyl-4'-methyleneglutamic acid (1) having the following chemical structure:

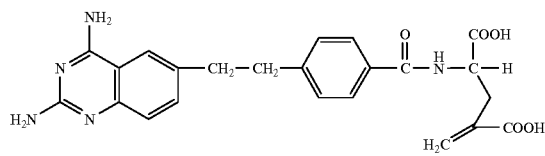

2. 4-Amino-4-deoxy-10-methyl-5,8,10-trideazapteroyl-4'-methyleneglutamic acid (1a) having the following chemical structure:

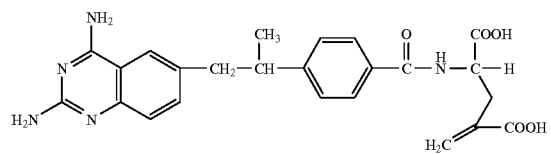

3. 4-Amino-4-deoxy-10-ethyl-5,8,10-trideazapteroyl-4'-methyleneglutamic acid (1b) having the following chemical structure:

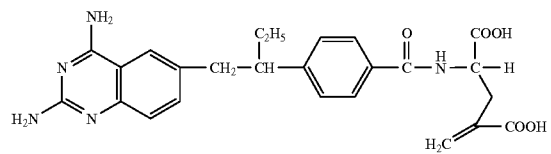

4. 4-Amino-4-deoxy-5,8-dideazapteroyl-4'-methyleneglutamic acid (1c) having the following chemical structure:

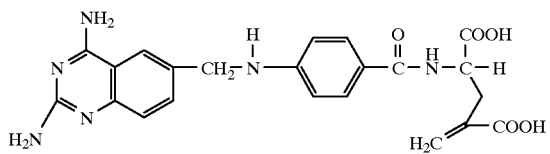

5. 4-Amino-4-deoxy-10-methyl-5,8-dideazapteroyl-4'-methyleneglutamic acid (1d) having the following structure:

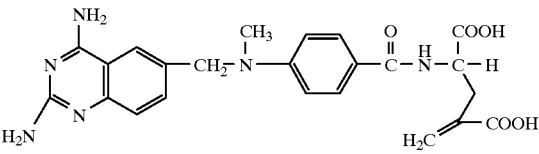

6. A pharmaceutical composition for the treatment of neoplastic growth that responds to antifolates a therapeutically effective and non toxic amount of 4-amino-4-deoxy-5,8,10-trideaza-pteroyl-4'-methylene glutamic acid (1) with or without a pharmaceutically acceptable carrier, diluent or anti-tumor agent to inhibit the said neoplastic growth.

7. A pharmaceutical composition for the treatment of neoplastic growth that responds to antifolates a therapeutically effective and non toxic amount of 4-amino-4-deoxy-10-methyl-5,8,10-trideaza-pteroyl-4'-methyleneglutamic acid (1a) with or without a pharmaceutically acceptable carrier, diluent or anti-tumor agent to inhibit the said neoplastic growth.

8. A pharmaceutical composition for treating neoplastic growth that responds to antifolates a therapeutically effective and non toxic amount of 4-amino-4-deoxy-10-ethyl-5,8,10-trideaza-pteroyl-4'-methyleneglutamic acid (1b) with or without a pharmaceutically acceptable carrier, diluent or anti-tumor agent to inhibit the said neoplastic growth.

9. A pharmaceutical composition for the treatment of neoplastic growth that responds to antifolates a therapeutically effective and non toxic amount of 4-amino-4-deoxy-5,8-dideaza-pteroyl-4'-methyleneglutamic acid (1c) with or without a pharmaceutically acceptable carrier, diluent or anti-tumor agent to inhibit the said neoplastic growth.

10. A pharmaceutical composition for the treatment of neoplastic growth that responds to antifolates a therapeutically effective and non toxic amount of 4-amino-4-deoxy-10-methyl-5,8-dideazapteroyl-4'-methyleneglutamic acid (1d) with or without a pharmaceutically acceptable carrier, diluent or anti-tumor agent to inhibit the said neoplastic growth.

11. A pharmaceutical composition for the treatment of inflammation caused by allergens or auto-immune response a therapeutically effective and non toxic amount of 4-amino-4-deoxy-5,8,10-trideazapteroyl-4'-methyleneglutamic acid (1) with or without a pharmaceutically acceptable carrier or diluent to ameliorate the said inflammation.

12. A pharmaceutical composition for the treatment of inflammation caused by allergens or auto-immune response a therapeutically effective and non toxic amount of 4-amino-4-deoxy-10 -methyl-5,8,10-trideazapteroyl-4'-methyleneglutamic acid (1a) with or without a pharmaceutically acceptable carrier or diluent to ameliorate the said inflammation.

13. A pharmaceutical composition for the treatment of inflammation caused by allergens or auto-immune response a therapeutically effective and non toxic amount of 4-amino-4-deoxy-10-ethyl-5,8,10-trideaza-4'-methyleneglutamic acid (1b) with or without a pharmaceutically acceptable carrier or diluent to ameliorate the said inflammation.

14. A pharmaceutical composition for the treatment of inflammation caused by allergens or auto-immune response a therapeutically effective and non toxic amount of 4-amino-4-deoxy-5,8-dideazapteroyl-4'-methyleneglutamic acid (1c) with or without a pharmaceutically acceptable carrier or diluent to ameliorate the said inflammation.

15. A pharmaceutical composition for the treatment of inflammation caused by allergens or auto-immune response a therapeutically effective and non toxic amount of 4-amino-4-deoxy-10-methyl-5,8-dideazapteroyl-4'-methyleneglutamic acid (1d) with or without a pharmaceutically acceptable carrier or diluent to ameliorate the said inflammation.

16. A process for treating neoplastic growth that responds to antifolates which comprises administering orally or parenterally to a warm blooded animal having evidence of neoplastic growth a therapeutically effective and non toxic amount of 4-amino-4-deoxy-5,8,10-trideaza-pteroyl-4'-methyleneglutamic acid (1) with or without a pharmaceutically acceptable carrier, diluent or antitumor agent to inhibit the said neoplastic growth.

17. A process for treating neoplastic growth that responds to antifolates which comprises administering orally or parenterally to a warm blooded animal having evidence of neoplastic growth a therapeutically effective and non toxic amount of 4-amino-4-deoxy-10-methyl-5,8,10-trideazapteroyl-4'-methyleneglutamic acid (1a) to inhibit the said neoplastic growth.

18. A process for treating neoplastic growth that responds to antifolates which comprises administering orally or parenterally to a warm blooded animal having evidence of neoplastic growth a therapeutically effective and non toxic amount of 4-amino-4-deoxy-10-ethyl-5,8,10-trideaza-4'-methyleneglutamic acid (1b) with or without a pharmaceutically acceptable carrier, diluent or antitumor agent to inhibit the said neoplastic growth.

19. A process for treating neoplastic growth that responds to antifolates which comprises administering orally or parenterally to a warm blooded animal having evidence of neoplastic growth a therapeutically effective and non toxic amount of 4-amino-4-deoxy-5,8-dideazapteroyl-4'-methyleneglutamic acid (1c) with or without a pharmaceutically acceptable carrier, diluent or anti-tumor agent to inhibit the said neoplastic growth.

20. A process for treating neoplastic growth that responds to antifolates which comprises administering orally or parenterally to a warm blooded animal having evidence of neoplastic growth a therapeutically effective and non toxic amount of 4-amino-4-deoxy-10-methyl-5,8-didezapteroyl-4'-methyleneglutamic acid (1d) with or without a pharmaceutically acceptable carrier, diluent or anti-tumor agent to inhibit the said neoplastic growth.

21. A process for treating inflammatory disease caused by allergens or autoimmune response which comprises of administering orally or parenterally to a warm blooded animal having evidence of inflammation a therapeutically effective and non toxic amount of 4-amino-4-deoxy-5,8,10-trideazapteroyl-4'-methyleneglutamic acid (1) with or without a pharmaceutically acceptable carrier or diluent to ameliorate the said inflammation.

22. A process for treating inflammatory disease caused by allergens or auto-immune response which comprises of administering orally or parenterally to a warm blooded animal having evidence of inflammation a therapeutically effective and non toxic amount of 4-amino-4-deoxy-10-methyl-5,8,10-tridezapteroyl-4'-methyleneglutamic acid (1a) with or without a pharmaceutically acceptable carrier or diluent to ameliorate the said inflammation.

23. A process for treating inflammatory disease caused by allergens or autoimmune response which comprises administering orally or parenterally to a warm blooded animal having evidence of inflammation a therapeutically effective and non toxic amount of 4-amino-4-deoxy-10-ethyl-5,8,10-trideazapteroyl-4'-methyleneglutamic acid (1b) with or without a pharmaceutically acceptable carrier or diluent to ameliorate the said inflammation.

24. A process for treating inflammatory disease caused by allergens or autoimmune response which comprises of administering orally or parenterally to a warm blooded animal having evidence of inflammation a therapeutically effective and non toxic amount of 4-amino-4-deoxy-5,8-dideazapteroyl-4'-methyleneglutamic acid (1c) with or without a pharmaceutically acceptable carrier or diluent to ameliorate the said inflammation.

25. A process for treating inflammatory disease caused by allergens or autoimmune response which comprises of administering orally or parenterally to a warm blooded animal having evidence of inflammation a therapeutically effective and non toxic amount of 4-amino-4-deoxy-10-methyl-5,8-dideazapteroyl-4'-methyleneglutamic acid (1d) with or without a pharmaceutically acceptable carrier or diluent to ameliorate the said inflammation.

26. A pharmaceutical composition for the treatment of asthma a therapeutically effective and non toxic amount of 4-amino-4-deoxy-5,8,10-trideazapteroyl-4'-methyleneglutamic acid (1d) with or without a pharmaceutically acceptable carrier or diluent to ameliorate asthma.

27. A pharmaceutical composition for the treatment of asthma a therapeutically effective and non toxic amount of 4-amino-4-deoxy-10-methyl-5,8,10-trideazapteroyl-4'-methyleneglutamic acid (1a) with or without a pharmaceutically acceptable carrier or diluent to ameliorate the asthma.

28. A pharmaceutical composition for the treatment of asthma a therapeutically effective and non toxic amount of 4-amino-4-deoxy-10-ethyl-5,8,10-trideaza-4'-methyleneglutamic acid (1b) with or without a pharmaceutically acceptable carrier or diluent to ameliorate the asthma.

29. A Pharmaceutical composition for the treatment of asthma a therapeutically effective and non toxic amount of 4-amino-4-deoxy-5,8-dideazapteroyl-4'-methyleneglutamic acid (1c) with or without a pharmaceutically acceptable carrier od diluent to ameliorate the asthma.

30. A pharmaceutical composition for the treatment of asthma a therapeutically effective and non toxic amount of 4-amino-4-deoxy-10-methyl-5,8-dideazapteroyl-4'-methyleneglutamic acid (1d) with or without a pharmaceutically acceptable carrier or diluent to ameliorate the asthma.

31. 4-Amino-4-deoxy-5,8,10-trideazapteroyl-4'-methyleneglutamic acid (1) having the following chemical structure in which the 4-methyleneglutamate moiety has the "L" configuration:

32. 4-Amino-4-deoxy-5,8,10-trideazapteroyl-4'-methyleneglutamic acid (1) having the following chemical structure in which the 4-methyleneglutamate moiety has the "D" configuration:
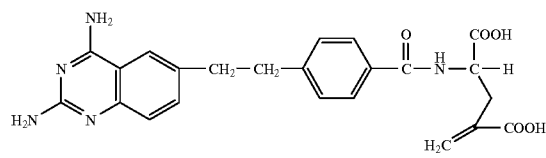
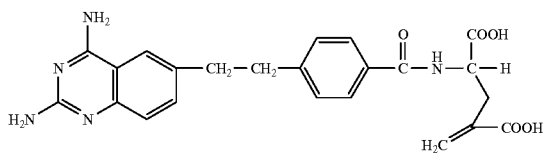
* * * * *

UNITED STATES PATENT AND TRADEMARK OFFICE
CERTIFICATE OF CORRECTION

PATENT NO. : 5,912,251
DATED : June 15, 1999
INVENTOR(S) : Nair, Madhavan G.

It is certified that error appears in the above-identified patent and that said Letters Patent is hereby corrected as shown below:

Column 1,
Line 5, insert new heading, -- CROSS-REFERENCE TO GOVERNMENT GRANTS --.
Line 6, insert new paragraph, -- Research performed in support of this invention was supported in part by PHS Grant Number CA27101. The U.S. Government may therefore have certain rights in the invention. --.

Signed and Sealed this

Sixth Day of September, 2005

JON W. DUDAS
*Director of the United States Patent and Trademark Office*